United States Patent
Carrez et al.

(10) Patent No.: US 9,234,616 B2
(45) Date of Patent: Jan. 12, 2016

(54) NON-DRIP, DIRECT-FLOW CONNECTORS WITH SECURE LOCKING

(75) Inventors: Jean-Luc Carrez, Ecouen (FR); Laurent Barre, Ecouen (FR); Marie-Hélène Pech, Paris (FR)

(73) Assignee: Vygon (FR)

( * ) Notice: Subject to any disclaimer, the term of this patent is extended or adjusted under 35 U.S.C. 154(b) by 0 days.

(21) Appl. No.: 14/235,966

(22) PCT Filed: Jul. 26, 2012

(86) PCT No.: PCT/EP2012/064669
§ 371 (c)(1),
(2), (4) Date: Jan. 29, 2014

(87) PCT Pub. No.: WO2013/017518
PCT Pub. Date: Feb. 7, 2013

(65) Prior Publication Data
US 2014/0209197 A1    Jul. 31, 2014

(30) Foreign Application Priority Data
Jul. 29, 2011    (FR) ..................................... 11 56955

(51) Int. Cl.
*F16L 37/38* (2006.01)
*F16L 37/02* (2006.01)
(Continued)

(52) U.S. Cl.
CPC ................. *F16L 37/02* (2013.01); *A61M 39/10* (2013.01); *F16L 29/005* (2013.01); *F16L 37/38* (2013.01); *A61M 2039/1033* (2013.01); *A61M 2039/267* (2013.01); *Y10T 137/9029* (2015.04)

(58) Field of Classification Search
CPC ........... F16L 37/02; F16L 37/28; F16L 37/38; F16L 29/005; F16L 29/02; A61M 2039/267; A61M 2039/1027; A61M 203/1072

USPC .......... 137/614.03–614.05; 251/149.1, 149.6; 604/249, 256
See application file for complete search history.

(56) References Cited

U.S. PATENT DOCUMENTS 5,492,147 A * 2/1996 Challender et al. ...... 137/614.05
6,113,068 A * 9/2000 Ryan .......................... 251/149.6
(Continued)

FOREIGN PATENT DOCUMENTS

EP    0544581 A1    6/1993
WO   0020070 A1    4/2000
(Continued)

OTHER PUBLICATIONS

French Preliminary Search Report for Application No. FR 1156955 dated Jun. 22, 2012.
(Continued)

*Primary Examiner* — Kevin Lee
(74) *Attorney, Agent, or Firm* — Lerner, David, Littenberg, Krumholz & Mentlik, LLP (57) ABSTRACT

The invention relates to a male connector for a liquid circuit, comprising: a distal connection piece comprising a tubular part that defines a passage; a proximal connection piece; a joining member extending in a fixed and co-axial manner in the tubular part of the distal connection piece, the joining member being formed by a tubular body on which is fixed, at a free end, a cylindrical valve which is elastically deformable and closed at a distal end by a valve thickness traversed by a slit; and a sliding ring mounted on the tubular body, the sliding ring being movable between an inactive position, in which it encapsulates the walls of the valve, leaving the distal end of the valve free, and a connection position, in which it is situated at a distance from the distal end of the valve and exposes all or part of the lateral walls of the valve.

29 Claims, 9 Drawing Sheets

(51) Int. Cl.
*F16L 29/00* (2006.01)
*A61M 39/10* (2006.01)
*A61M 39/26* (2006.01)

(56) References Cited

U.S. PATENT DOCUMENTS

| | | | |
|---|---|---|---|
| 6,168,137 B1 * | 1/2001 | Paradis | 251/149.6 |
| 8,048,039 B2 * | 11/2011 | Carlyon et al. | 251/149.6 |
| 8,671,966 B2 * | 3/2014 | Pascal et al. | 251/149.1 |
| 2003/0209681 A1 | 11/2003 | Leinsing et al. | |
| 2008/0183155 A1 | 7/2008 | Funamura et al. | |

FOREIGN PATENT DOCUMENTS

| | | |
|---|---|---|
| WO | 2006062912 A1 | 6/2006 |
| WO | 2008052140 A2 | 5/2008 |
| WO | 2011101389 A1 | 8/2011 |

OTHER PUBLICATIONS

International Search Report for Application No. PCT/EP2012/064669 dated Aug. 30, 2012.

* cited by examiner

NON-DRIP, DIRECT-FLOW CONNECTORS WITH SECURE LOCKING

CROSS REFERENCE TO RELATED APPLICATIONS

The present application is a national phase entry under 35 U.S.C. §371 of International Application No. PCT/EP2012/064669, filed Jul. 26, 2012, published in French, which claims priority from French Patent Application No. 1156955, filed Jul. 29, 2011, the disclosures of which are incorporated by reference herein.

BACKGROUND OF THE INVENTION

The invention relates to a connector for a fluid circuit, particularly for medical use.

Such a secure connector is known from document EP 0 544 581, comprising a distal entry cone of the female "Luer" type designed to be connected with a device having a compatible and complementary male "Luer" type connector. The distal entry cone is plugged by a septum or membrane having a flush surface which is easily cleanable to remove germs or bacteria prior to making a connection. The septum protects a tube which, once the connection is made, extends partially into the hole in the male "Luer" type connector which is connected to it. Once connected, the connector of document EP 0 544 581 has a straight tubular passage and reduced dead volume. The connector described in document EP 0 544 581 is a secure female connector.

A secure connector set for a liquid circuit was then proposed in international application PCT/EP 2011/052315, including a male connector and a female connector, each including a proximal coupler and a distal coupler. The distal coupler of each of the connectors defines a passage and includes a tubular part wherein extends coaxially a connection member fixedly mounted on the proximal coupler, and an elastically deformable, substantially tubular membrane, closed at a distal end by a membrane body. The membrane of each connector is movable between a plugging position, wherein the membrane sealingly covers a free end of the connection member, and an connecting position wherein the connection member passes through the membrane. Moreover, the tubular part of the distal coupler of the male connector is designed to be inserted, upon connection, into the tubular part of the distal coupler of the female connector, such that in a plugging position, for each of the male and female connectors, the membrane sealingly blocks the passage in the distal coupler.

This connection set has the advantage of reducing the number of steps needed for its assembly by an operator. Moreover, it includes easily cleanable connection means, particularly at the distal parts of the connectors, in that the membranes are flush with the distal end of the connectors.

Moreover, document WO 2006/062912 describes a sealing male Luer connector which can be fixed to a standard female Luer valve for the purpose of opening a flow channel between the two. To this end, the male connector includes a rigid housing having a distal end provided with a rigid male Luer connector and a proximal end at which a proximal seal is formed. The distal end of the housing includes a valve seat. A resilient biasing member is positioned inside the compartment, this member biasing an actuator into contact with the valve seat so as to prevent fluid flow through the male connector. Upon engagement with a female connector, the actuator is moved in the proximal direction to open the distal valve and then the proximal seal. A partial vacuum is formed within the male connector upon disengagement with the female connector, so as to aspirate liquids on the external surface of the distal end of the male connector into the male tip.

Document WO 00/20070, for its part, describes a needleless penetrating point connector having a hollow spike, a female Luer, a flexible and resilient spike boot having a tip and a spring portion extending above the spike, a centering member covering a portion of the spike boot and a resilient swabbable septum placed between the centering member and one end of the female Luer. The hollow spike and the female Luer are fastened together and terminate the assembly. The length of the Luer and/or the length of the spike are such that, when a male Luer is pushed into the female Luer, it urges a pressure on the septum and presses it toward the spike so that the tip portion of the boot is pierced by the tip of the spike. When the septum is further compressed, it extends above the spike, so that the cavity of the point is in fluid communication with the male Luer hub. This injection port causes minimal reflux and the septum constitutes a swabbable double antibacterial barrier over the spike.

Finally, document WO 2008/052140 describes a medical connector including a rigid housing, a rigid internal member positioned inside the housing and comprising at least one lateral opening, and a hollow flexible member positioned inside the housing, a protrusion whereof is designed to penetrate into the lateral opening.

It is important for these medical liquid circuit connectors to limit or eliminate the risks of drop formation at the outlet of the connectors at the time of their separation. Indeed, the products transferred through these connectors are generally more or less dilute medicines, which can therefore be dangerous for exposed users or patients, as can be the case for those preparing medicines. The formation of drops at the outlet of the connectors can also be the source of cross-contamination in the preparation of the medicines themselves.

SUMMARY OF THE INVENTION

One object of the invention is therefore to propose a novel assembly of male and female connectors with secure connection for a fluid circuit, the membrane and the body whereof are perfectly cleanable, while limiting or even eliminating the formation of drops upon separation of the connectors.

Secondarily, another object of the application is to propose a connector assembly for a fluid circuit which limits the risks of deterioration of the fluids passing through it, such as the risks of destruction of packed red blood cells.

For this purpose, the invention proposes a male connector for a liquid circuit, including:
  a distal hub including a tubular portion defining a passage,
  a proximal hub,
  a connection member extending fixedly and coaxially into the tubular portion of the distal hub, said connection member consisting of a tubular body onto which is fastened, at a free end, an elastically deformable cylindrical valve closed at a distal end by a thickness of valve with a slit passing through it, and
  a sliding ring mounted on the tubular body, said sliding ring being movable between an inactive position, wherein it encapsulates the walls of the valve while leaving free the distal end of said valve, and a connection position wherein it is situated at a distance from the distal end of the valve and uncovers all or part of the sidewalls of the valve.

Certain preferred but not limiting aspects of the male connector of the invention are the following:

it also includes a biasing means supported between the sliding ring and the tubular body and designed to return the sliding ring to its rest position;

the valve sealingly closes the free end of the tubular body;

the valve also exhibits at least one blind groove leading to the tubular body, said groove extending substantially parallel to the slit, coaxial with the tubular body, or around the slit;

the valve is overmolded onto the tubular body;

the distal end of the valve has a concave surface;

in the rest position, a distal surface of the distal end of the valve is flush with a distal surface of the distal end of the sliding ring;

the valve also includes, at the slit, an extra radial thickness extending coaxially with the tubular body;

the extra thickness has a shape of an ellipse, the minor diameter whereof is substantially equal to an internal diameter of the sliding ring, and a major diameter measures a few tenths of a millimeter more than the minor diameter;

the distal hub encapsulates the tubular body and the sliding ring so as to leave only their respective distal ends free;

the sliding ring also includes a gasket extending between the sliding ring and the distal hub;

the gasket is positioned in a radial cavity of said sliding ring, or overmolded onto said sliding ring;

the distal end of the tubular body includes a shoulder designed to accommodate the valve, so that an outer surface of the sidewalls of the valve and of the tubular body is continuous;

the tubular body defines an internal channel of substantially constant cross-section;

the distal hub additionally includes locking means;

the locking means are of the bayonet type;

a distal end of the distal hub has centering walls aligned with the distal hub;

the tubular body also has a slit extending parallel to the slit in the valve from its distal end toward its proximal end, so as to define two lateral legs; and the slit of the valve is beveled toward the tubular body.

According to a second aspect, the invention proposes a manufacturing method for a male connector conforming to the invention, including the steps consisting of:

providing a tubular body;

fastening the valve to a distal end of the tubular body;

fastening the tubular body to the proximal hub;

mounting the sliding ring on the distal end of the tubular body; and fastening the distal hub to the tubular body.

Certain preferred but not limiting aspects of the tubular body conforming to the invention are the following:

it also includes a step during which a slit is made in the valve after fastening the valve onto the distal end of the tubular body; and the valve is attached by overmolding onto the tubular body.

According to a third aspect, the invention proposes a connection assembly for a liquid circuit including a male connector conforming to the invention and a female connector, said female connector including:

a distal hub, and a proximal hub, the distal hub including a tubular portion wherein extends coaxially a connection member fixedly mounted on the proximal hub, and a deformable cylindrical membrane elastically closed at a distal end by a septum through which passes a slit, and movable between a plugging position wherein the membrane sealingly covers a free end of the connection member, and a connection position wherein the connection member passes through the membrane and the valve.

Certain preferred but non-limiting aspects of the assembly are the following:

a shape and dimensions of the valve of the male connector are substantially equal to a shape and to dimensions of the membrane, so that during connection of the male connector with the female connector the valve is able to penetrate into the distal end of the distal hub of the female connector;

the distal end of the membrane has a convex surface, while the distal end of the valve has a concave surface, the concavity of the surface of the distal end of the valve corresponding to the convexity of the surface of the distal end of the membrane;

the female connector and the male connector each include complementary bayonet locking means;

the dimensions and the shape of the distal hub of the female connector are substantially identical with the dimensions and the shape of the sliding ring, so that when connecting the male connector with the female connector the distal end of the female connector is able to penetrate into the distal end of the distal hub of the male connector; and the tubular body of the male connector also has a slit extending parallel to the slit of the valve from its distal end toward its proximal end so as to define two lateral legs, and wherein the lateral legs of the male connector deform elastically during penetration of the connection member of the female connector into the slit of the valve of the male connector.

According to a fourth aspect, the invention proposes the use of a connector assembly conforming to the invention, including the steps consisting of:

placing the distal end (120) of the female connector (100) against the distal end (10) of the male connector (1), so that the valve (40) is in contact with the membrane (130);

inserting the distal hub (140) of the female connector (100) into the distal hub (10) of the male connector (1), by pushing the female connector (100) toward the male connector (1), so that the valve (40) penetrates into the distal end of the distal hub (140) of the female connector (100) and the distal hub (10) of the male connector (1) displaces the sliding ring (50) toward the proximal hub of the male connector (1) until the connection member (124) of the female connector (100) passes through both the membrane (130) and the valve (40); and locking the assembly.

Other features, objects and advantages of the present invention will be more apparent upon reading the detailed description which follows, and with reference to the appended drawings given by way of non-limiting examples and in which:

DETAILED DESCRIPTION

Figure 1:
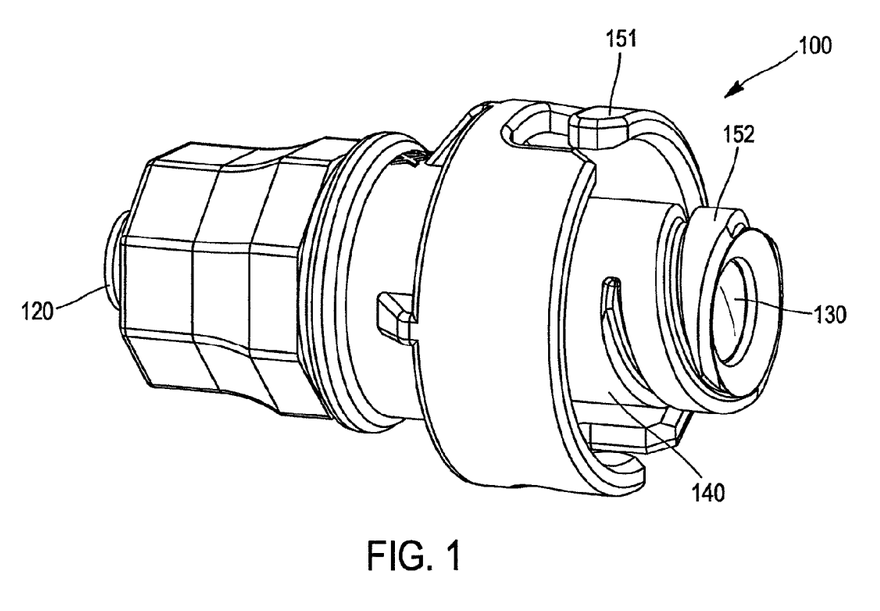
FIG. 1 is a perspective view of an embodiment of a female connector which can be used in an assembly conforming to the invention.
Figure 2:
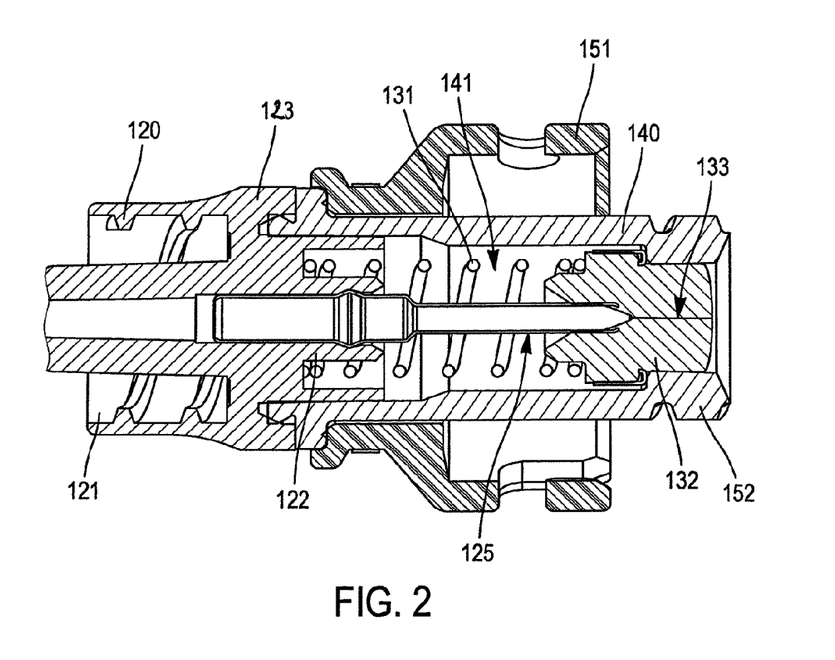
FIG. 2 is a sectional view of the female connector of FIG. 1.

Referring to FIGS. 1 and 2, we will first of all describe a female connector 100 according to the invention.

The female connector 100 comprises a proximal hub 120, an elastically deformable, substantially tubular membrane 130 and a distal hub 140 attached to the proximal hub 120.

The proximal hub 120 has a generally tubular shape and comprises a proximal end which includes, here, a connectable entry 121 of the female "Luer lock" type. As a variant embodiment, this connectable entry 121 is of the male "Luer lock" type. It extends in the distal direction into a hollow body 122.

The hollow body 122 of the proximal hub 120 is terminated, in the distal direction, by a circular shaped flange 123 coaxially topped by a hollow connection tube 124 which extends, protruding from the proximal hub 120 in the distal direction. The hollow tube 124 terminates in a free distal end 125 and constitutes a connection member.

We will now describe in more detail the membrane 130 of the connector 100.

This membrane 130 has a distal end 132 and comprises elastic means 131.

Here the elastic means 131 are a spring 131, for example of the helical compression spring type, extending up to the distal end 132. They are designed to be supported on the proximal hub 120 and to press the distal end 132 of the membrane 130 so that the latter goes into its rest (inactive) position, in which it plugs a distal end of the passage 141.

The distal end 132 of the membrane 130 is a septum having a distal surface which is convex overall, through which passes a slit coaxial with the connection tube 124.

Thus the female connection 100 comprises a membrane 130 which is encapsulated in the tubular portion of the distal hub 140, so that only the distal surface through which the slit passes is accessible to an operator. This also allows, in the rest position, radial clamping of the membrane 130, and in particular of the distal end 132 of the latter, accomplished by a wall of the tubular portion of the distal hub 140: better sealing and resistance to back-pressure are then obtained.

On its perimeter, preferably on the proximal portion, the distal hub 140 comprises a locking means 150. Here, the locking means is female and of the bayonet type and includes a skirt 151 provided with grooves designed to cooperate with the male lugs of a complementary bayonet locking means. In the embodiment illustrated in FIGS. 1 and 2, the distal end 152 of the distal hub 140, which is surrounded by the skirt 151, is threaded so as to constitute a connectable entry of the female "Luer lock" type. For this purpose, the distal portion of the skirt 151 is shortened and offset so that the distal end face 151 is radially accessible. Thus, a female locking means is obtained which can be connected either to the lugs of a male bayonet locking means or to a complementary male "Luer lock" locking means.

These locking means 150 will be detailed later in the description.

A more detailed description of a connector similar to the connector 100 is supplied in document PCT/EP 2011/052315 cited above, which can be referred to this end.

We will at present describe a male connector 1 according to the invention with reference to FIGS. 3 through 8B.

Figure 3:
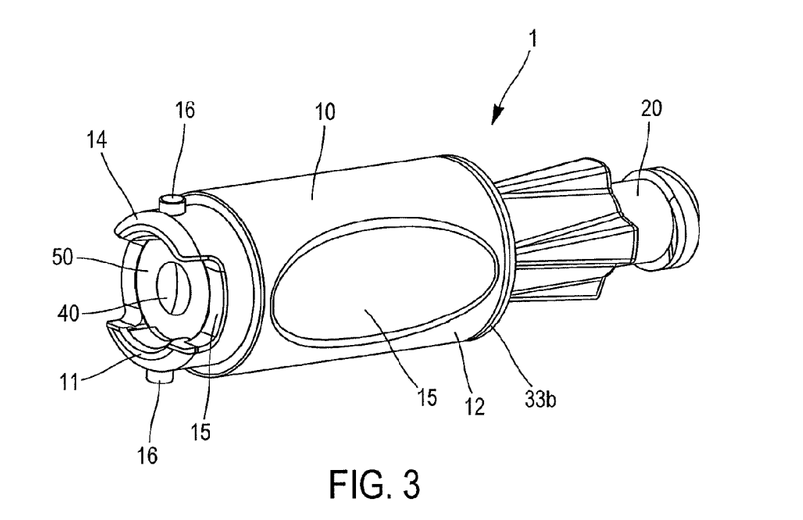
FIG. 3 is a perspective view of an embodiment of a male connector conforming to the invention.
Figure 4:
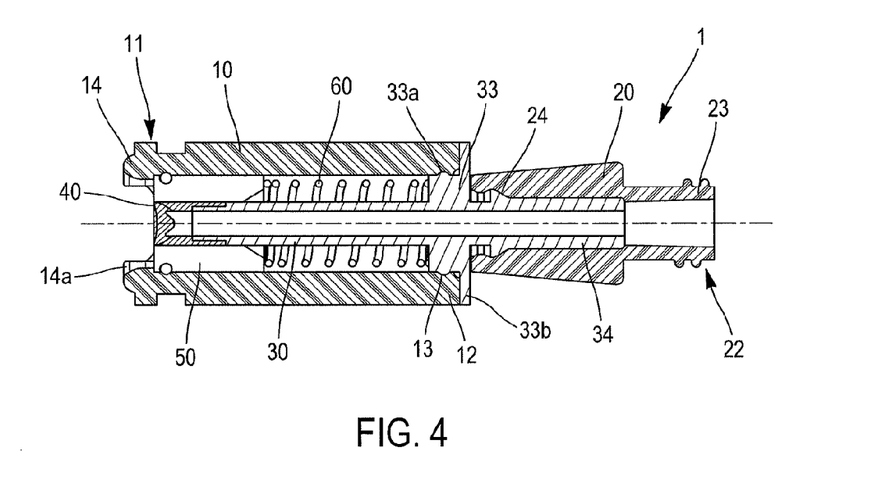
FIG. 4 is a sectional view of the male connector of FIG. 3.

The male connector 1 includes a distal hub 10 comprising a tubular portion defining a passage, a proximal hub 20 and a connection member 30.

The connection member 30 extends into the passage 11 of the distal hub 10, coaxially with the tubular portion thereof. It has the form of a body which is tubular overall, forming an internal channel 31 of circular cylindrical shape overall, and has a valve 40 at a distal end 32.

The tubular body 30 is inserted into the distal hub 10 in such a way that the valve 40 is adjacent to the distal end 11 of the distal hub.

It also includes a radial bulge 33 designed to engage with the proximal end of the distal hub 12. For example, the bulge 33 has the shape of a disk extending transversely to the axis of the tubular body, the outer diameter whereof is substantially equal to the inner diameter of the distal hub 10. The disk also has snap-in means 33a, for example a radial protrusion which can be annular, designed to cooperate with a groove 13 of complementary shape made in the inner face of the distal hub 10, and is extended by a collar 33b of greater diameter serving as a stop for the distal hub 10. Thus, when the tubular body 30 is inserted into the distal hub 10, the proximal end 12 of the distal hub 10 rests against the collar 33b serving as a stop and engages with the annular protrusion 33a, so that the distal hub 10 is blocked in translation relative to the tubular body 30.

Finally, the tubular body 30 extends in its proximal portion beyond the radial bulge 33 into a zone 34 for gripping the proximal hub 20. The gripping zone 34 includes a cylindrical body having, at an inner face, at least one connection member 34a. Preferably, the gripping zone 34 is a circular cylinder, the connection member 34a then taking the form of an annular protrusion. In this manner, the proximal hub 20 is fixed in translation on the tubular body 30 but free in rotation about it, so as to avoid accidental releases of the proximal hub 20 of the male connector 1.

Figure 5A:
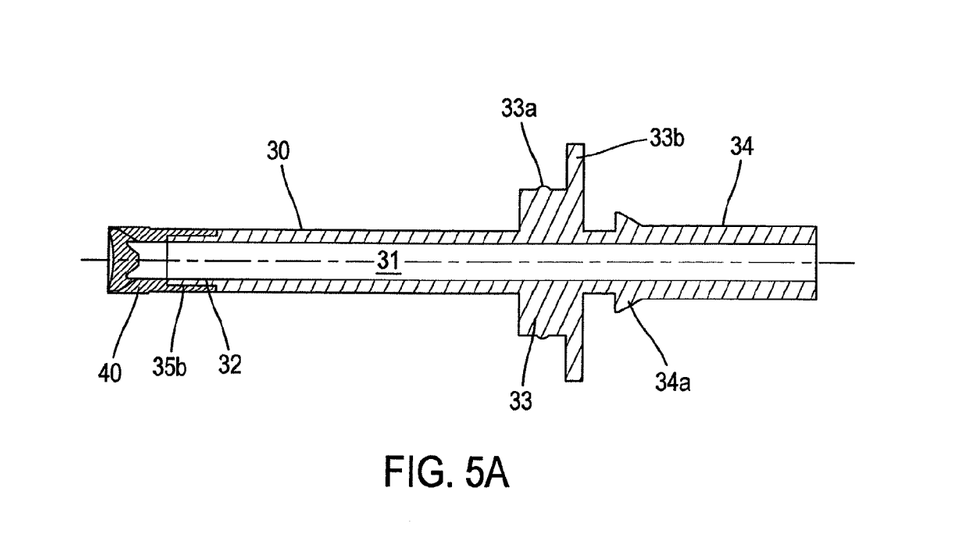
FIG. 5A is a sectional view of an exemplary embodiment of a tubular body on which is fastened a valve conforming to the invention.
Figure 5B:
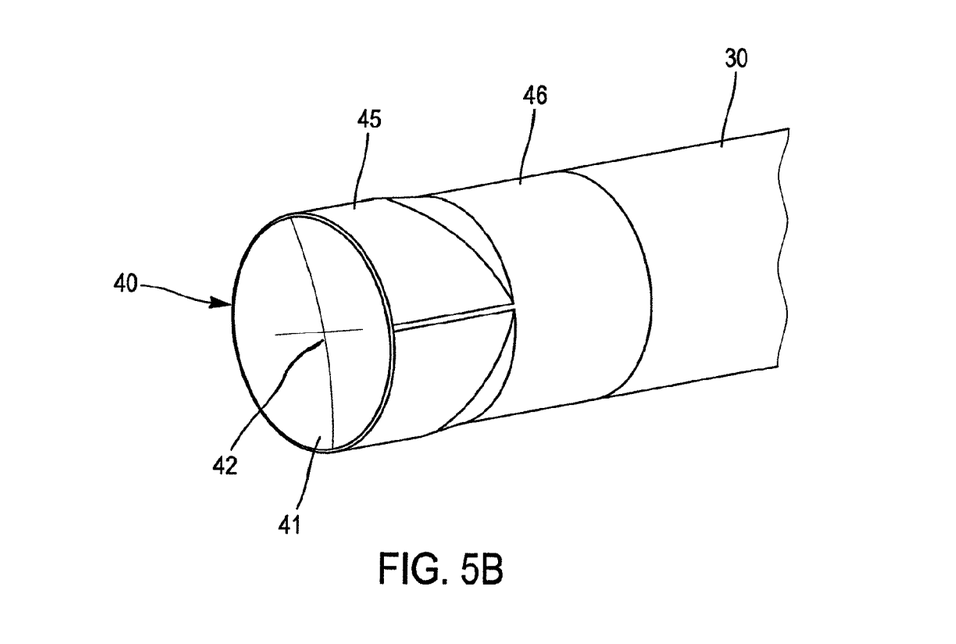
FIG. 5B is a perspective view of the distal portion of the exemplary embodiment of FIG. 5A.

The valve 40 of the tubular body 30 is an elastically deformable membrane, of cylindrical shape overall, and closed at a distal end 41 by a membrane. The outer diameter of the valve 40 is less than or equal to, preferably substantially equal to, the outer diameter of the membrane 130.

A slit 42 runs through the thickness of the membrane, leading to the tubular body 30. The distal end of the tubular body 32 and the slit 42 can be separated by an internal space 43 extending the internal channel 31.

The slit 42 can be straight or beveled in the direction of the tubular body 30, depending in particular on its manufacturing method.

Figure 6:
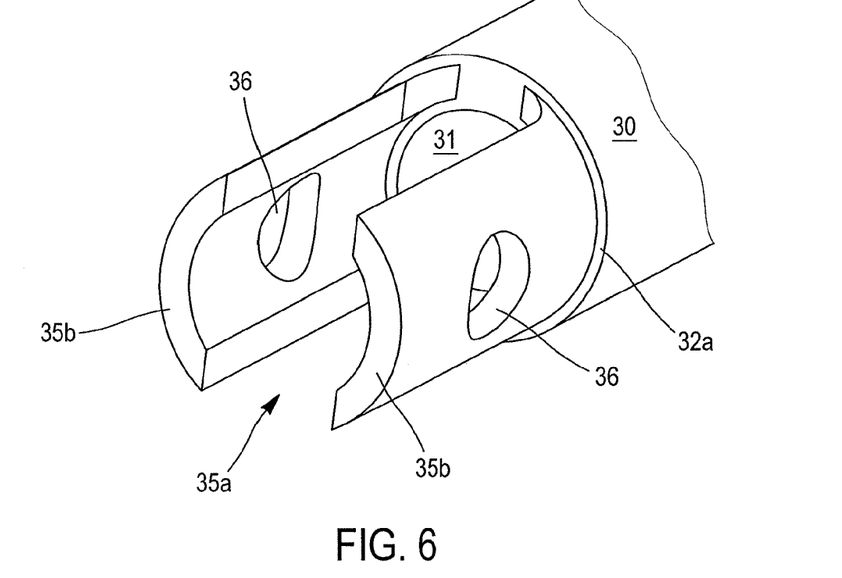
FIG. 6 is a perspective view of an embodiment of the distal portion of a tubular body conforming to the invention.

For example, the valve 40 is made of an elastomeric material allowing the tubular body 30 to be sealingly closed despite the presence of the slit 42. Typically, the valve 40 can be made of LSR (Liquid Silicone Rubber), while the tubular body 30 is made of a plastic material such as PBT (polybutylene terephthalate) plastic resin. It can then be overmolded onto the tubular body 30. In this case, in order to improve the connection between the valve 40 and the tubular body 30, the distal end of the tubular body 30 can in particular have one or more radial openings 36 passing through it. Moreover, the slit 42 is preferably made by cutting through the thickness of the membrane after fastening the valve 40 onto the tubular body 30, for example by means of a scalpel, so as to be precisely indexed with respect to the tubular body 30.

Advantageously, the distal end 32 of the tubular body 30, on which is fastened the valve 40, has an annular shoulder 32a formed by shrinking the wall of the tubular body 30 so as to accommodate the valve 30 without creating a discontinuity at the outer surface of the connection member. The valve 40 is then overmolded (or fastened) into this shoulder 32a over a thickness such that the outer wall 46 of the valve 40 and the tubular body 30 form a continuous surface which is smooth overall.

Figure 7A:
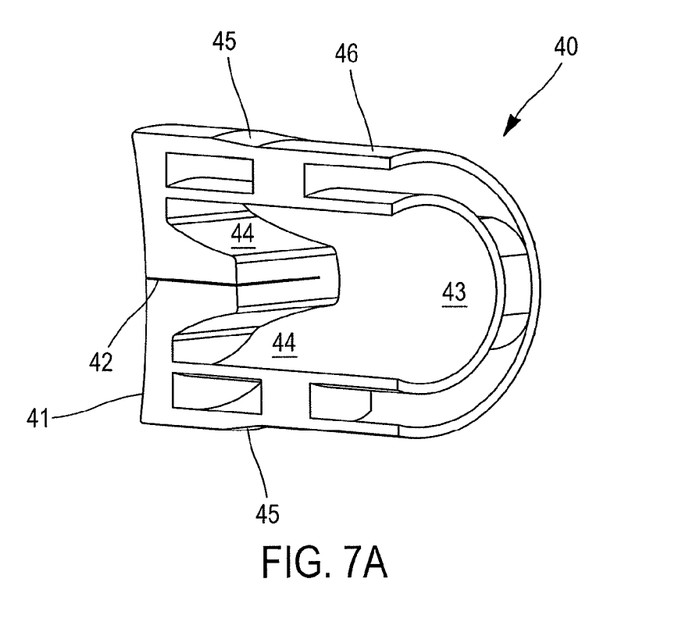
FIG. 7A is a perspective view of a section of an exemplary embodiment of a valve conforming to the invention.
Figure 7B:
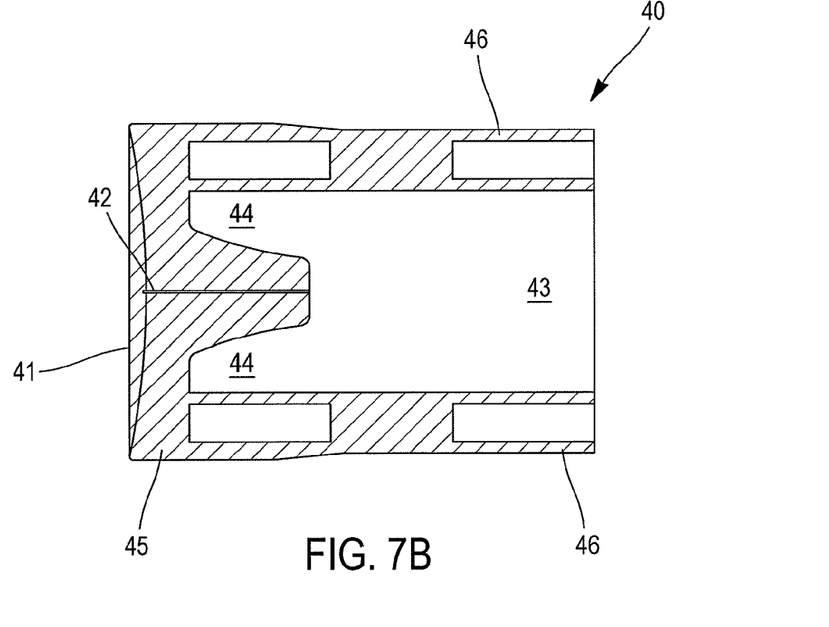
FIG. 7B is a sectional view of FIG. 7A.
Figure 7C:
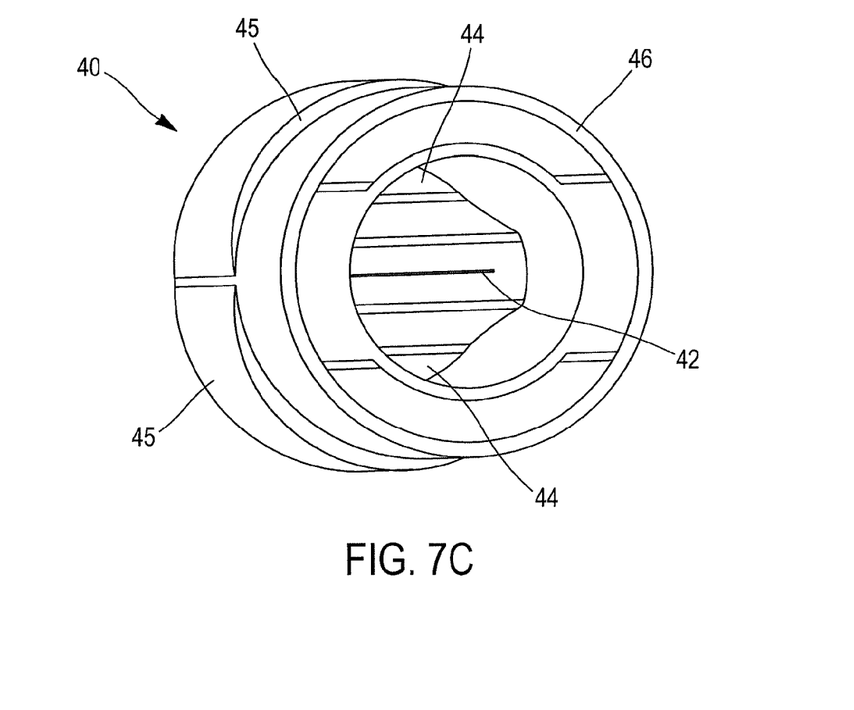
FIG. 7C is a perspective view of the proximal portion of a valve conforming to FIG. 7A.

According to one embodiment, the valve 40 includes in addition at least one blind groove 44 leading to the tubular body 30 and which is coaxial with the tubular body 30.

The groove 44 has a dual effect on the slit 42.

During the opening of the slit 42 by the introduction of an object from the distal end 41 thereof, as we will see later in the description, the groove 44 allows the slit 42 to open more easily, the edges of the slit 42 not being held back due to the empty space created by the groove 44.

Moreover, when the slit 42 is closed (and thus has not object such as the connection tube 124 passing through it), in the event of migration of fluid coming from the tubular body 30, the fluid enters the groove 44 and applies pressure on the edges of the slit which tends to push the edges of the slit 42 together. The slit 42 is therefore held closed and prevents the fluid from escaping, thus increasing the sealing of the connector 1.

The groove 44 can for example be of annular shape and extend around and at a distance from the slit, transverse to the axis of the tubular body 30. As a variant, the valve 40 includes two substantially rectilinear grooves 44 extending parallel to the slit 42, on either side thereof. This embodiment has the advantage of applying a more effective pressure to the slit 42, and hence of improving its resistance to counter-pressure. According to yet another variant, the grooves 44 are curved and on either side of the slit.

Finally, according to one embodiment, the distal end 41 of the valve 40 is a concave surface. The surface of the distal end of the membrane 130 of the female connector 100 being of convex shape, this allows the distal end of the valve 40 to perfectly fit the surface of the membrane 130, and thus to limit leakage of fluid when the connectors 1 and 100 are connected together. Preferably, the concavity of the distal end 41 of the valve 40 matches the convexity of the distal end of the membrane 130.

As a variant, the surface of the distal end of the membrane 130 of the female connector 100 is of concave shape; the distal end 41 of the valve 40 is then a convex surface with matching convexity.

Figure 8A:
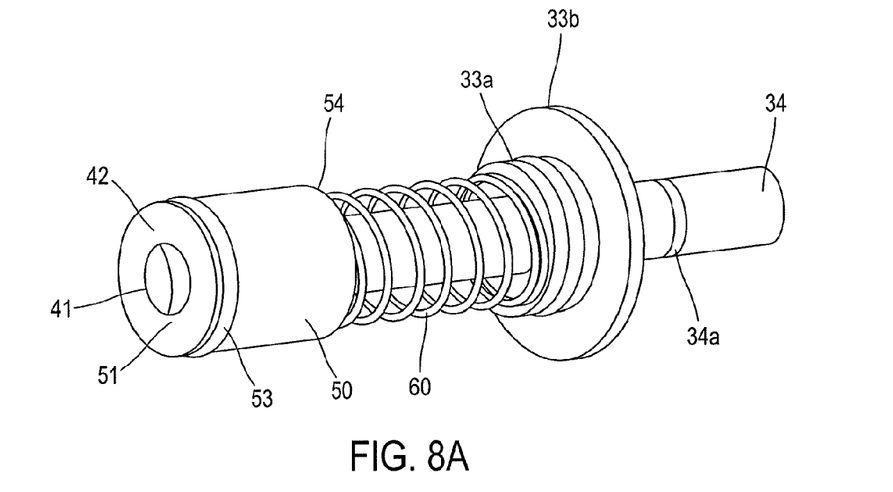
FIG. 8A is a perspective view of an assembly including the tubular body and the valve of FIG. 5B, an exemplary embodiment of a sliding ring and an exemplary embodiment of an elastic means conforming to the invention.
Figure 8B:
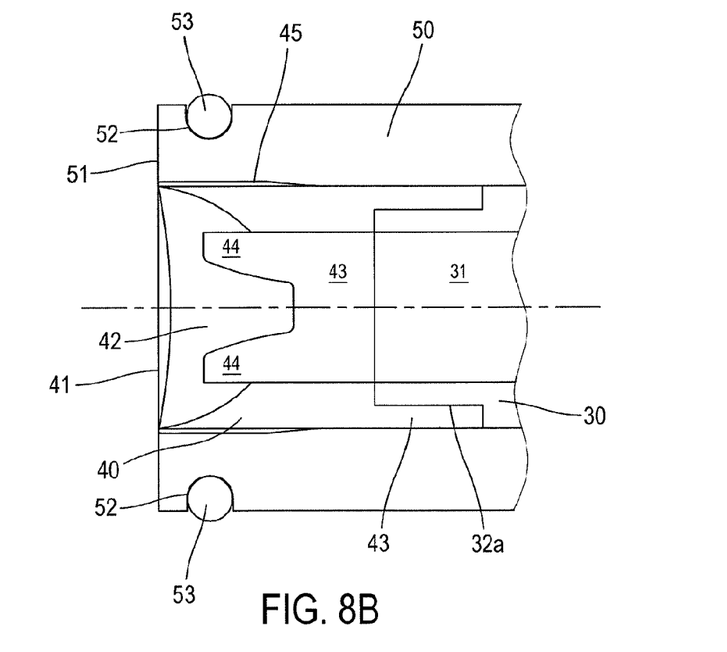
FIG. 8B is a sectional view of the distal portion of the assembly of FIG. 7.

The male connector 1 also includes a sliding ring 50 mounted on the tubular body 30, movable between an inactive, so-called rest position and a connection position.

In the rest position, the ring 50 encapsulates the sidewalls 46 of the valve 40, leaving free only its distal end 41. Preferably, the distal end 41 of the valve 40 is flush with the surface of the distal end 51 of the ring 50, so as to minimize edges and facilitate the cleaning of the connector 1. This position is particularly illustrated in FIGS. 3, 4, 8A, 8B and 10.

Figure 11:
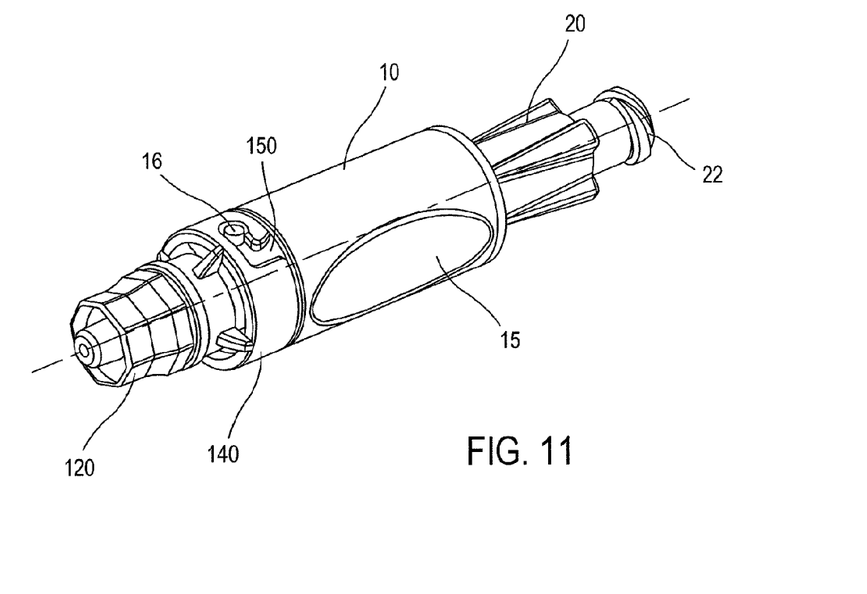
FIG. 11 is a side view of a female connector and of a male connector connected and locked.
Figure 12:
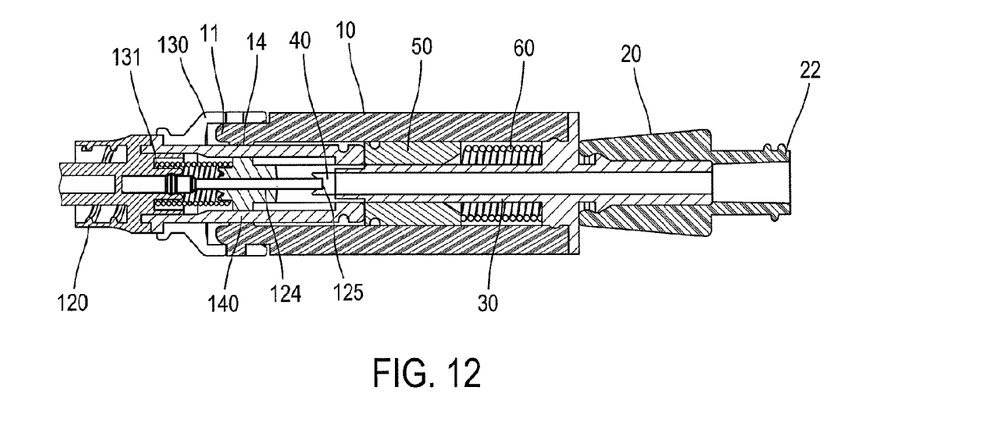
FIG. 12 is a sectional view of the female and male connectors of FIG. 11.
Figure 13:
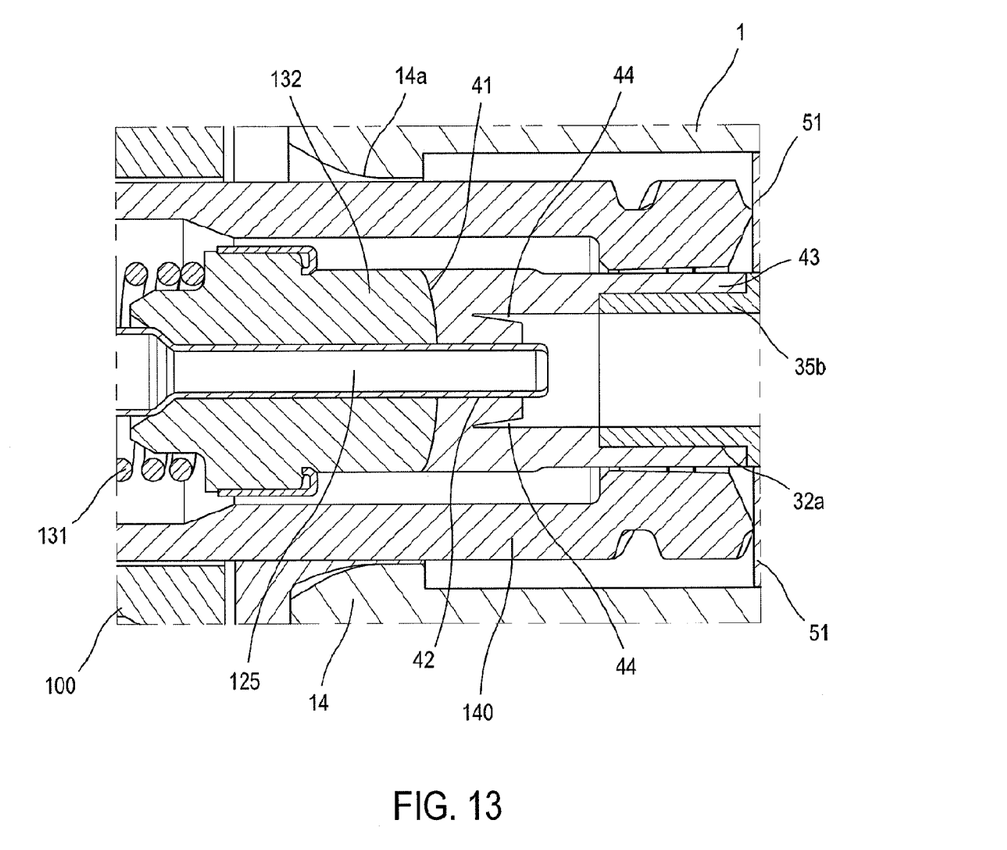
FIG. 13 is a detail view of the connection of the female connector with the male connector of FIG. 12.

In the connection position, illustrated in particular in FIGS. 11 through 13, the ring 50 is located at a distance from the distal end 41 of the valve 40 and exposes all or a portion of the valve 40.

Advantageously, the inner diameter of the ring 50 is substantially equal to the outer diameter of the tubular body 30 and of the valve 40.

The valve 40 can also have a slight thickening 45 (on the order of 5% of the total thickness of the valve 40) extending radially at its distal end 41, adjacent to the slit 42. In this manner, in the rest position, the ring 50, the inner diameter whereof is slightly smaller than the outer diameter of the valve 40 at the thickened portion 45, exerts a centripetal radial force on the valve 40 and the slit 42. Consequently, at rest, the ring 50 further increases the resistance to counter-pressure of the valve 40.

Moreover, the thickened portion 45 allows passage of fluid between the ring 50 and the valve 40 to be prevented.

In the embodiment illustrated in the figures, the thickened portion 45 is present only on either side of the slit 42, so that the pressure is only exerted on either side thereof, this improving its resistance to counter-pressure. For example, the thickened portion can have the shape of an ellipse, the minor diameter whereof (at the ends of the slit 42) is substantially equal to the inner diameter of the ring 50, while the major diameter (at the edges of the slit 42) measures a few tenths of a millimeter more than the minor diameter.

The outer diameter of the sliding ring 50 is preferably substantially equal to the inner diameter of the distal hub 10, so as to limit passage of fluid between the ring 50 and the hub 10. If necessary, the outer surface of the ring 50 can also include an annular groove 52 designed to receive an O-ring gasket 53, so as to further improve the sealing of the connector 1 and avoid the introduction of products such as disinfectants.

The O-ring 53 can for example be made of an elastomeric material such as LSR silicone.

As a variant, the O-ring 53 is overmolded directly onto the ring 50, with or without the annular groove 52.

The inner surface of the ring 50, which is in contact with the valve 40, is preferably smooth, and for this purpose can have undergone surface treatment so as to facilitate the movement of the ring 50 along the tubular body 30. For example, the inner face of the ring 50 can be silicone-treated.

Sliding of the ring 50 is further improved by the fact that the outer surface of the valve 40 and of the tubular body 30 is continuous and of constant diameter.

The ring 50 can for example be made of a PBT type plastic material.

The male connector 1 also includes a biasing means 60, designed to return the sliding ring 50 to its rest position.

In the embodiments illustrated in the figures, the biasing means 60 is an elastic spring coaxial with the tubular body 30, extending between the proximal face 54 of the sliding ring 50 and the distal face of the radial cavity 33 of the tubular body 30. In this manner, when the sliding ring 50 is moved in toward its connection position, the spring 60 exerts on the ring 50 a biasing force tending to push the ring in the opposite direction, toward the distal end of the connector 1.

This embodiment of the biasing means 60 is not limiting, however. It can also consist of a bellows operating in compression, etc.

Preferably, when the return means 60 is at rest, the sliding ring 50 is also in its rest position.

According to an embodiment illustrated in particular in FIG. 6, the tubular body 30 can also be slit from its distal end toward its proximal end. Preferably, the slit 35a in the tubular body 30 extends over only a portion of the body 30, for example in the distal portion which is in contact with the valve 40, and confers on the distal portion of the body a certain radial elasticity.

Advantageously, the slit 35a of the tubular body 30 is substantially parallel to the slit 42 of the valve 40.

Moreover, according to a preferred embodiment, the slit 35a is made in the tubular body 30 in such a way that the edges forming said slit 35a are distant from one another. The distal portion of the tubular body 30 therefore consists of two lateral legs 35b separated by the slit 35a, as illustrated in FIG. 6. Thus, when the valve 40 is fastened on the distal portion of the tubular body 30 by overmolding, this overmolding is then accomplished in such a way that the sidewalls 46 of the valve 40 fill the slit 35a and cover the legs 35b of the tubular body 30.

Advantageously, in the rest position of the sliding ring 50, the lateral legs 35b of the tubular body 30 are radially constrained by the ring 50 toward the internal channel 31 of the tubular body 30, so as to further improve the sealing of the slit 42 of the valve 40, which improves the resistance to counter-pressure of the valve 40.

Moreover, the space created by the slit 35a allows the creation of a slit 42 of arbitrary width, without it being limited by the distal portion of the tubular body 30.

We will see hereafter in the description the function of this slit 35a in the male connector 1.

The distal hub 10 is fastened on the tubular body 30 and the sliding ring 50, so that its distal end 12 rests against and engages with the radial thickening 33 and it encapsulates the sliding ring 50 and the valve 40. The distal hub 10 is therefore immobile in translation with respect to the tubular body 30. According to the embodiment of the snap-in means 33a, the distal hub can however be mobile in rotation about the tubular body 30, for example when the protrusion 33 and the groove 13 are annular and extend coaxially with the tubular body 30.

Figure 10:
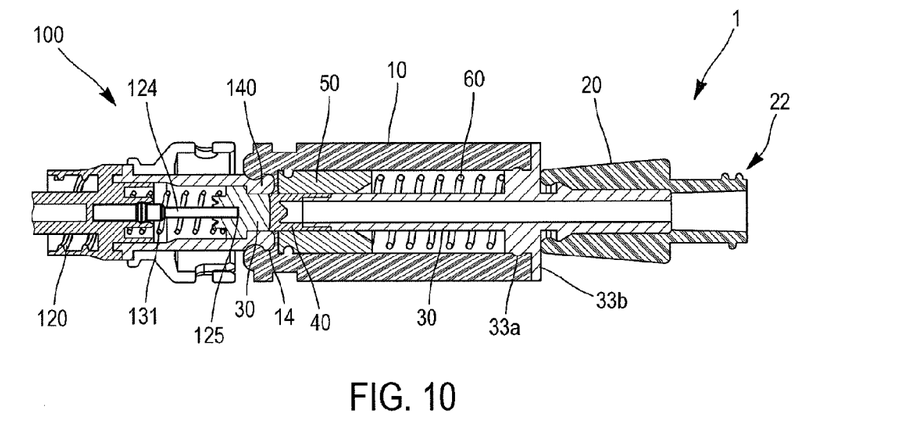
FIG. 10 is a sectional view of the female and male connectors of FIG. 9.

In the embodiment illustrated in FIGS. 10, 12 and 13, the distal hub 10 also includes, at its distal end 11, at least one curved centering wall 14, which extends the outer surface of the distal end of the hub 10. Such a centering wall 14 makes it possible to facilitate the alignment on the same axis of the male connector 1 and the corresponding female connector while they are being connected, which guarantees their correct operation and avoids deteriorating them.

Preferably, the distal hub 10 includes at least two facing centering walls 14, separated radially by two notches 15, so as to facilitate the cleaning of the flush distal surfaces 41 and 51 of the valve 40 and the sliding ring 50.

The internal face of the centering walls 14 can in addition include sloping protrusions 14a extending radially inward in order to further improve guidance of the female connector 100.

The distal end 11 of the distal hub 10 also includes locking means 16, preferably of the bayonet type. Here, the locking means are two male lugs 16 of a bayonet system, each extending from an outer surface of a centering wall 14.

As a variant (not illustrated in the figures), the distal end 11 of the distal hub 10 includes a distal skirt having female bayonet locking means.

This type of locking means 16 has the advantage, compared with conventional threaded type locking means, of having surfaces which are smooth overall so that access to them is easy and they are therefore easy to clean. Moreover, they provide simple and secure locking of the male connector 1 with a corresponding female connector 100.

Moreover, the distal hub 10 also includes means 15 for holding the male connector 1. Here they are two in number and take the form of two cavities which extend radially on either side of the distal hub 10. These grasping means 15 make it possible to firmly hold the male connector 1 when connecting it with the female connector 100.

As for the proximal hub 20, it comprises at its proximal end 22 a conventional connectable entry 23 of the female "Luer lock" type, capable of being assembled to a syringe (or any other suitable medical equipment) having a connection end of the male "Luer" "slip" (smooth) or "lock" (locking) type, in a manner not shown in the figures. This connectable entry 23 is preferably sealed against pressures of up to 3 bars. To this end, for example, the outer diameter of the proximal portion 34 of the tubular body 30 is slightly larger than the inner diameter of the proximal hub 20 at its connectable entry 23.

Moreover, the proximal hub 20 includes a circular cylindrical gripping member 24 coaxial with the tubular body 30, designed to cooperate with the corresponding gripping member 34a corresponding to the gripping zone of the tubular body 30. In this manner, the proximal hub 20 is fixed in translation on the tubular body 30, while remaining mobile in rotation about the axis thereof. Any unintended rotary motion of the male connector 1 (for example during disconnection of the male connector 1 and a female connector 100 by rotation of said connectors 1 and 100 so as to disconnect their bayonet locking means 16) is therefore compensated by the free rotation of the distal hub 20 with respect to the tubular body 30, thus avoiding accidental disconnections of the male connector 1 and of the syringe.

We will now describe a method for using a connector assembly including a male connector 1 conforming to the invention and a corresponding female connector.

Here the female connector corresponds to the connector 100 described previously with reference to the appended FIGS. 1 and 2 and detailed in document EP 2011/05231. This is not limiting, however.

During a first step, the distal ends of the two connectors 1 and 100 are cleaned. This cleaning is all the easier because the valve 40 and the membrane 130 of the male 1 and female 100 connectors, respectively, are flush with the distal ends of the distal hubs so that the distal surface of each connector 1, 100 is smooth. If necessary, replacement of conventional threads by bayonet locking means 16, 150 also facilitates this cleaning, thanks to the offset of the skirt 151 of the female connector 100, which allow easy access to the threads of the distal end 152 of the connector 100, as well as the absence of conventional threads on the locking means of the male connector.

Figure 9:
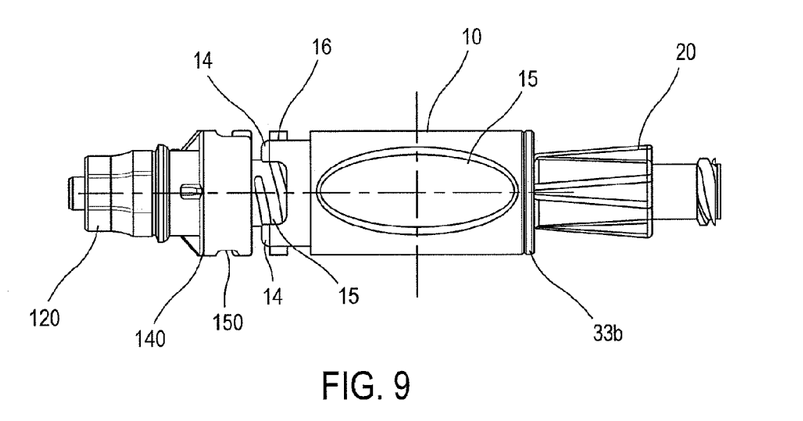
FIG. 9 is a side view of a female connector and of a male connector in contact prior to assembly.

Once the cleaning is accomplished, the operator brings the respective distal ends of the male and female 100 connectors into contact. To this end, he applies the concave surface of the valve 40 to the convex surface of the membrane 130 and the distal end of the distal hub 140 onto the distal end 51 of the sliding ring 50, as illustrated in FIGS. 9 and 10, then connects the assembly.

It will be noted that the distal hubs 140 and 10 of the two connectors, female 100 and male 1, are structurally similar (aside of course from their respective locking means): the membrane 130 and the valve 40 are indeed flush with the distal end of their distal hub 140, 10 so that coupling/uncoupling of the male connector 1 and the female connector 100 is accomplished with only one axial motion. It is in fact no longer necessary to attach the distal hubs 140, 10 of the female 100 and male 1 connectors before beginning to push the connectors together, the two operations being performed simultaneously thanks to the structure of the distal hubs 140, 240.

Here, the operator places the respective locking means of the male and female connector facing one another, then locks them. In the exemplary embodiment illustrated, the operator places for example the lugs 16 of the male connector 1 facing the corresponding grooves 150 of the female connector 100, the slides the connectors 100, 1 relative to one another by pushing the male connector 1, supported by the centering means 14 of its distal hub 10, toward the female connector 100.

During this manipulation, the valve 40 of the male connector 1 presses on the distal end of the membrane 130 of the female connector 100, while the distal hub 140 of the female connector 100 presses on the sliding ring 50 of the male connector. Consequently, the valve 40 and a portion of the tubular body 30 of the male connector 1 penetrate into the distal hub 140 of the female connector 100, while the distal end of the distal hub 140 of the male connector 100 penetrates into the distal end 11 of the distal hub 10 of the male connector 1.

To this end, the valve 40 forces the elastic means 131 to compress, so that the membrane 30 moves back toward its connection position, which forces the distal end 125 of the hollow tube 124 to cross, through the slit 133, the septum situated at the distal end of the membrane 130. Simultaneously, the distal end of the distal hub 140 of the female connector 100, which is resting against the sliding ring 50, forces the return means 60 to compress, and thus moves the sliding ring 50 toward its connection position. The valve 40 and the tubular body 30, on the other hand, do not move with respect to the distal hub 10 and to the proximal hub 20 of the male connector 1.

In addition, the valve 40 does not open as long as the distal end 125 of the hollow tube 124 of the female connector 100 does not pass through the membrane, particularly due to the axial stiffness conferred by the distal portion of the tubular body 30 on which is fixed the valve 40.

According to a preferred embodiment, the material and the thickness of the valve 40 are selected so that it is sufficiently strong when it pushes the membrane 130 so as not to open and sag toward the tubular body 30. The object, in fact, is to that the valve 40 be capable of transmitting to the membrane 130 of the female connector 100 the thrust force applied by the operator on the gripping means 14 to force the membrane 130 of the female connector 100 to move back toward its connection position wherein the distal end 125 of the connection tube 124 passes through the membrane 130.

This resistance to sagging of the valve 40 is also reinforced axially by the fact that the valve 40 is fastened on the distal portion of the tubular body 30. What is more, the presence of the lateral legs 35b further reinforces, if necessary, the axial stiffness of the valve 40.

Once the distal end 125 of the tube 124 has passed through the membrane thickness of the distal end of the membrane 130, this distal end 125 of the tube 124 is in supporting contact with the valve 40 of the male connector 1. Given that the operator continues to press the male 1 and female 100 connectors together, the distal end 125 of the tube 124 presses on the distal end 41 of the valve 40, finally penetrating into the slit 42 of the valve 40. Indeed, at this stage, the elastic means are already strongly compressed and exert a return force greater than that of the edges of the slit 42, so that these yield and spread apart to allow passage of the connection tube 124.

The pressure continues until the distal end 125 of the tube 124 of the female connector 100 is in fluid connection with the tubular body 30 of the male connector 1. At this point, the connection and a fluid passage are accomplished between the male 1 and female 100 connectors.

It will be noted here that the distal end 125 of the connection tube 124 of the female connector 100 does not necessarily penetrate into the distal end of the tubular body 30. In fact, it is sufficient for it to be adjacent to it, as illustrated in FIGS. 12 and 13.

The operator then turns the connectors relative to one another so as to position the lugs 16 of the male connector to their limit in the corresponding grooves 150 of the female connector 100, and to lock the assembly of the connectors 100, 1.

In order to facilitate the penetration of the distal end 125 of the connection tube 124 of the female connector 100 into the slit 42 of the valve 40, the tubular body 30 opens along its slit 35a. This opening is facilitated by the presence of the lateral legs 35b, which confer flexibility (in the direction perpendicular to the plane of the slit 35a) to the distal end of the tubular body 30 and allow its elastic deformation under the influence of the connection tube 124 on the valve 40. In this manner, when the edges of the slit 42 finally spread open to allow passage to the distal end 125 of the connection tube 124, the valve 40 sags partially and the lateral legs 35b of the tubular body 30 deform elastically so as to move away from one another, thus reducing the axial resistance that they exert on the valve 40 so as to facilitate passage of the distal end 125.

It will be noted that, at this stage of the connection, the sliding ring 50 is near to its connection position, so that it does not prevent this opening. On the other hand, in the rest position, the sliding ring 50 tends to hold the slit 35a of the tubular body 30 closed.

The spreading of the edges of the slit 42 can also be facilitated by the groove 44, if any.

When disconnecting, the operator unlocks the locking means of the connectors 1 and 100, for example by turning the connectors relative to one another in the case of bayonet locking means, then separates the connectors 1, 100 with the help of the thrust of the elastic means 131 and of the return means 60. Gradually, the free end 125 of the connection tube 124 emerges from the valve 40, which allows the slit 42 to close again. This closing of the slit 42 is further improved thanks to the elastic return of the lateral legs 35b, which tends to bring the lateral legs 35b into the initial rest position, wherein the lateral legs 35b exert a radial force toward the inner channel 31 on the slit 42.

The membrane 130 then gradually covers again the free end 125 of the tube 124 until it sealingly plugs it: the membrane 130 is then in its rest position.

Concurrently, the valve 40 and the tubular body 30 emerge from the distal hub 140 of the female connector 100, which for its part gradually emerges from the distal hub 10 of the male connector 1, thus allowing the sliding ring 50 to return to its rest position.

During connection or disconnection, sealing is ensured throughout the operation. In fact, sealing is provided by contact, at all times, between the membrane 130 and the valve 40.

Moreover, the risks of drop formation at the time of disconnection are strongly limited, even eliminated. Indeed, only a single member now passes through the membrane 130 and the valve 40, to wit the connection tube 124, which moreover is very narrow, while in the prior art the male connector also includes a connection tube which passes through both membranes. The connection tube of prior art male connectors is moreover relatively large compared with the connection tube 124, so that the slit in the membrane 130 and the slit 42 in the valve 40 must open wider to allow it to pass.

By using a narrow connection tube 124 for the female connector 100, the slit 133 of the membrane 130 and of the valve 40 therefore open much less than in the prior art, so that it becomes much more difficult for the fluid to enter it, thus reducing the formation of drops at the time of disconnection.

Naturally, it is possible to apply numerous modifications to the invention without departing from the scope thereof.

The invention claimed is:

1. A male connector for a liquid circuit, including:
   a distal hub including a tubular portion defining a passage,
   a proximal hub,
   a connection member extending fixedly and coaxially within the tubular portion of the distal hub, said connection member consisting of a tubular body whereon is fastened, at a free end, a cylindrical, elastically deformable valve closed at a distal end, the distal end having a thickness and a slit passing through the thickness, and
   a sliding ring mounted on the tubular body, said sliding ring being movable between an inactive position, wherein the sliding ring encapsulates walls of the valve while leaving free the distal end of said valve, and a connection position wherein the sliding ring is situated at a distance from the distal end of the valve and exposes all or a portion of sidewalls of the valve.

2. The male connector according to claim 1, also including a biasing means supported between the sliding ring and the tubular body and designed to bias the sliding ring toward its rest position.

3. The male connector according to claim 1, wherein the valve sealingly closes the free end of the tubular body.

4. The male connector according to claim 1, wherein the valve also has at least one blind groove leading to the tubular body, said groove extending substantially parallel to the slit, coaxially with the tubular body, or around the slit.

5. The male connector according to claim 1, wherein the valve is overmolded onto the tubular body.

6. The male connector according to claim 1, wherein the distal end of the valve has a concave surface.

7. The male connector according to claim 1, wherein, in the rest position, a distal surface of the distal end of the valve is flush with a distal surface of the distal end of the sliding ring.

8. The male connector according to claim 1, wherein the valve also includes, at the slit, a radial thickening extending coaxially to the tubular body.

9. The male connector according to claim 8, wherein the radial thickening has a shape of an ellipse, a minor diameter whereof is substantially equal to an inner diameter of the sliding ring and a major diameter whereof measures a few tenths of a millimeter more than the minor diameter.

10. The male connector according to claim 1, wherein the distal hub encapsulates the tubular body and the sliding ring so as to leave only their respective distal ends free.

11. The male connector according to claim 10, wherein the sliding ring also includes a seal extending between the sliding ring and the distal hub.

12. The male connector according to claim 11, wherein the seal is positioned in a radial cavity of said sliding ring, or overmolded onto said sliding ring.

13. The male connector according to claim 1, wherein the distal end of the tubular body includes a shoulder designed to accommodate the valve, so that an outer surface of the sidewalls of the valve and of the tubular body is continuous.

14. The male connector according to claim 1, wherein the tubular body defines an inner channel of substantially constant cross-section.

15. The male connector according to claim 1, wherein the distal hub also includes locking means.

16. The male connector according to claim 15, wherein the locking means are a bayonet type locking means.

17. The male connector according to claim 1, wherein a distal end of the distal hub has centering walls aligned with the distal hub.

18. The male connector according to claim 1, wherein the tubular body also has a slit extending parallel to the slit of the valve from its distal end toward its proximal end, so as to define two lateral legs.

19. The male connector according to claim 1, wherein the slit of the valve is beveled toward the tubular body.

20. A method for manufacturing a male connector according to claim 1, comprising:
   providing a tubular body;
   fastening the valve onto a distal end of the tubular body; and
   fastening the tubular body onto the proximal hub; characterized in the method for manufacturing a male connector further comprising the following steps:
   mounting the sliding ring on the distal end of the tubular body; and
   fastening the distal hub onto the tubular body.

21. The manufacturing method according to claim 20, further comprising a step during which the slit in the valve is formed after fastening the valve onto the distal end of the tubular body.

22. The manufacturing method according to claim 20, wherein the valve is fastened by overmolding onto the tubular body.

23. A connection assembly for a liquid circuit, including a male connector according to claim 1, and a female connector, said female connector including:
   a distal hub, and
   a proximal hub, the distal hub including a tubular portion wherein extends coaxially a connection member mounted fixedly on the proximal hub and an elastically deformable cylindrical membrane closed at a distal end by a septum through which passes a slit, movable between a plugging position wherein the membrane sealingly covers a free end of the connection member, and a connection position wherein the connection member passes through the membrane and the valve.

24. The connection assembly according to claim 23, wherein a shape and dimensions of the valve of the male connector are substantially equal to a shape and to dimensions of the membrane, so that when connecting the male connector with the female connector, the valve is able to penetrate into the distal end of the distal hub of the female connector.

25. Connection assembly according to claim 23, wherein the distal end of the membrane has a convex surface, while the distal end of the valve has a concave surface, the concavity of the surface of the distal end of the valve corresponding to the convexity of the surface of the distal end of the membrane.

26. The connection assembly according to claim 23, wherein the female connector and the male connector each include complementary bayonet locking means.

27. The connection assembly according to claim 23, wherein the dimensions and the shape of the distal hub of the female connector are substantially identical to the dimensions and to the shape of the sliding ring, such that during connection of the male connector with the female connector, the distal end of the female connector is able to penetrate into the distal end of the distal hub of the male connector.

28. The connection assembly according to claim 23, wherein the tubular body of the male connector also has a slit extending parallel to the slit of the valve from its distal end toward it proximal end to as to define two lateral legs, and wherein the lateral legs of the male connector deform elastically during penetration of the connection member of the female connector into the slit of the valve of the male connector.

29. Use of an assembly according to claim 23, including the steps consisting of:
- placing the distal end of the female connector against the distal end of the male connector so that the valve is in contact with the membrane;
- inserting the distal hub of the female connector into the distal hub of the male connector by pushing the female connector toward the male connector, so that the valve penetrates into the distal end of the distal hub of the female connector and the distal hub of the male connector moves the sliding ring toward the proximal hub of the male connector until the connection member of the female connector passes through both the membrane and the valve; and
- locking the assembly.

* * * * *